US00PP37094P2

(12) United States Plant Patent
Hung et al.

(10) Patent No.: US PP37,094 P2
(45) Date of Patent: Nov. 11, 2025

(54) ***ALOCASIA* PLANT NAMED 'HUTAAL29'**

(50) Latin Name: *Alocasia scalprum*
Varietal Denomination: HUTAAL29

(71) Applicant: Huta Green Company Limited, Hanoi (VN)

(72) Inventors: Pham Ngoc Hung, Hanoi (VN); Le Tuan Anh, Hanoi (VN)

(73) Assignee: Huta Green Company Limited, Hanoi (VN)

( * ) Notice: Subject to any disclaimer, the term of this patent is extended or adjusted under 35 U.S.C. 154(b) by 0 days.

(21) Appl. No.: 18/831,558

(22) Filed: Apr. 17, 2025

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

*Primary Examiner* — Susan Mccormick Ewoldt
(74) *Attorney, Agent, or Firm* — Samuel R. McCoy, Jr.

(57) ABSTRACT

'HUTAAL29' is a new and distinctive *Alocasia* plant which is characterized by foliage that exhibits an irregular variegation pattern with colors ranging from predominantly dark green with some amount of cream white to light yellow blotches to predominantly cream white to light yellow with dark green blotches, sporadic epidermal blistering on the adaxial foliar surface, pink foliar veins on the cream white to light yellow portions of the lamina, petioles that are greyed-red to greyed-purple when a large portion of the laminar surface is colored cream white to light yellow, and the stability of all characteristics from generation to generation.

3 Drawing Sheets

Latin name of the genus and species: The Latin name of the genus and species of the novel variety disclosed herein is *Alocasia scalprum.*

Variety denomination: The inventive variety of *Alocasia* disclosed herein has been given the variety denomination 'HUTAAL29'.

BACKGROUND OF THE INVENTION

Parentage: The new plant originated as a spontaneous, whole-plant mutation. The mutation was discovered at a plant tissue culture laboratory in Hanoi, Vietnam, in 2021, growing amongst a plurality of unnamed *Alocasia scalprum* in vitro plantlets (not patented) that typified the species. The mutation exhibited conspicuously variegated foliage relative to the parent which has solid green foliage. The mutated plantlet was isolated for further in vitro multiplication which yielded five additional variegated plantlets. During 2022, these five propagules were grown into mature plants in order to evaluate stability and uniqueness of the characteristics first observed. In 2023, it was determined that one of the five plants demonstrated a superior combination of unique and stable variegation and a uniform growth habit. The new plant was given the name, 'HUTAAL29'.

Asexual Reproduction: Asexual reproduction of the new cultivar 'HUTAAL29', by way of meristematic tissue culture micropropagation, was first initiated in October of 2023 in Hanoi, Vietnam. Three successive generations so produced have shown that the unique features of the instant plant cultivar are stable and reproduced true to type.

SUMMARY OF THE INVENTION

The cultivar 'HUTAAL29' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Alocasia* cultivar 'HUTAAL29'. These traits, in combination, distinguish 'HUTAAL29' as a new and distinct cultivar.

1. *Alocasia* 'HUTAAL29' exhibits narrowly cordate laminas borne on petioles that arise directly from the base of the plant; and
2. *Alocasia* 'HUTAAL29' exhibits petioles that are greyed-red to greyed-purple when a large portion of the laminar surface is colored cream white to light yellow; and
3. *Alocasia* 'HUTAAL29' exhibits mature foliage with an irregular variegation pattern, with colors ranging from predominantly dark green with some amount of cream white to light yellow blotches, to predominantly cream white to light yellow with dark green blotches; and
4. *Alocasia* 'HUTAAL29' exhibits sporadic blistering of the adaxial epidermis in the form of irregularly shaped, translucent-white blotches; and
5. *Alocasia* 'HUTAAL29' exhibits light greyed-purple midribs, generally appearing as a pink coloration, on those portions of the lamina that are colored cream white to light yellow.

BRIEF DESCRIPTION OF THE FIGURES

The photographs were taken using conventional techniques and although colors may appear different from actual colors due to light reflectance it is as accurate as possible by conventional photographic techniques.

BOTANICAL DESCRIPTION OF THE PLANT

Figure 1:
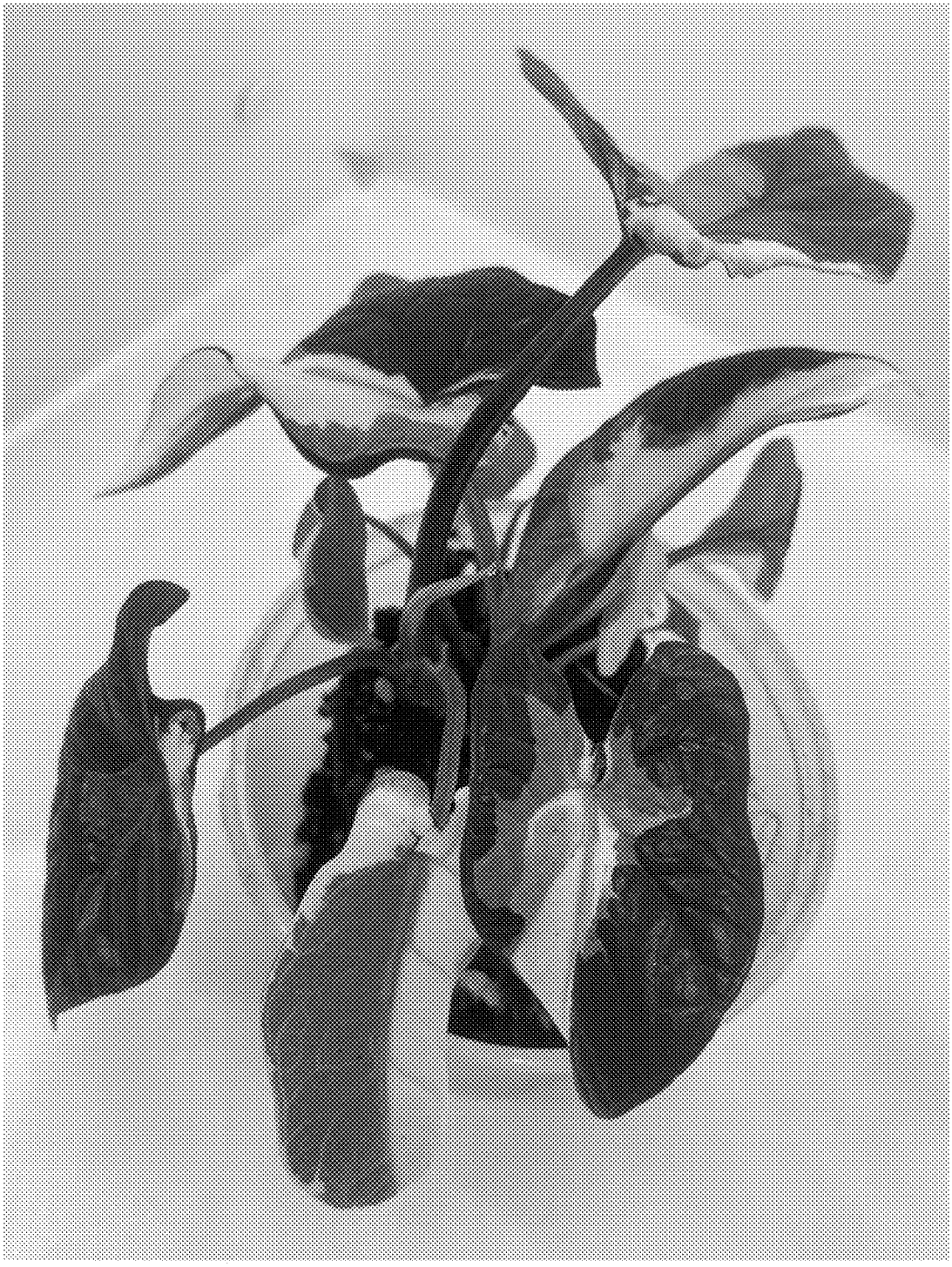
FIG. 1 shows, as nearly true as it is reasonably possible to make the same in color illustrations of this type, an exemplary mature plant of the new cultivar, 'HUTAAL29' grown in a 10 cm pot.
Figure 2:
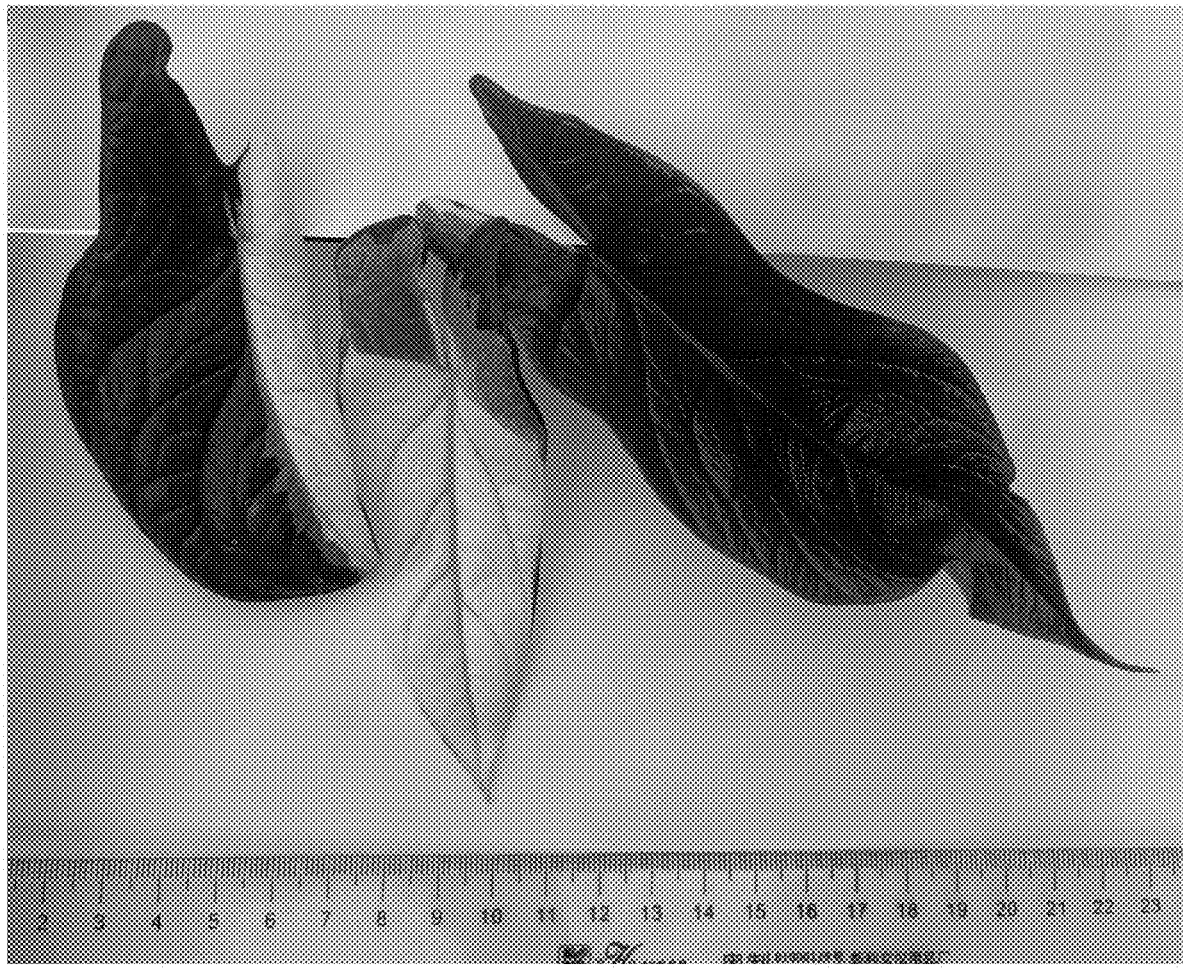
FIG. 2 shows the adaxial surface of the mature foliage of 'HUTAAL29'.
Figure 3:
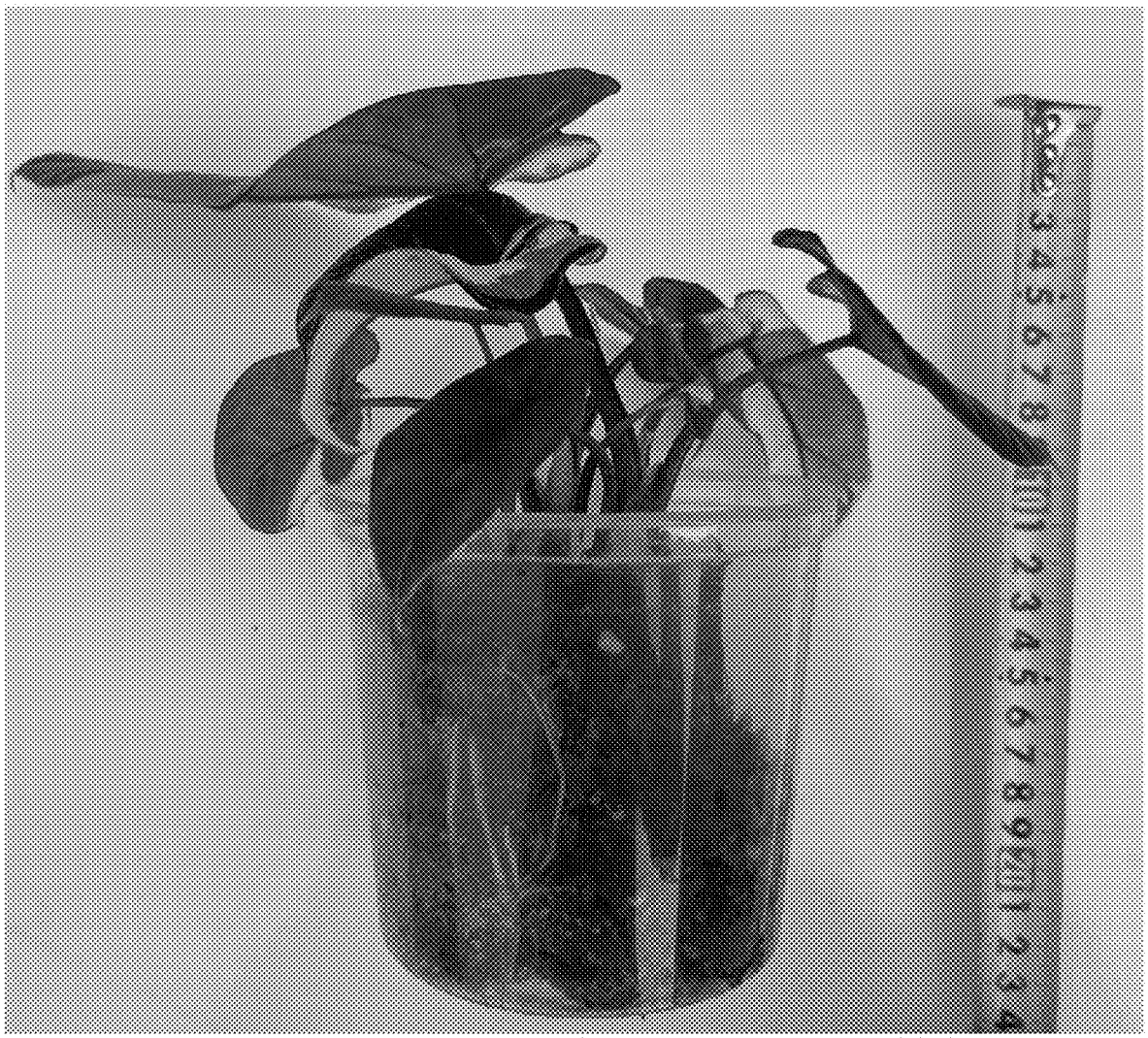
FIG. 3 shows the abaxial surface of the mature foliage of 'HUTAAL29'.

The following observations and measurements were made in June of 2024 and describe a 6-month-old 'HUTAHM06' plant grown in a 15 cm nursery container at a commercial greenhouse in Hanoi, Vietnam. Plants were produced using conventional greenhouse production protocols for *Alocasia* species which consisted of overhead irrigation twice a week, weekly applications of a liquid 20-20-20 fertilizer at an electroconductivity of 0.8, and anti-bacteria oxalinic acid at a rate of 375 parts-per-million and Imidacloprid insecticide at a rate 100 parts-per-million applied every week. Plants were grown under shade (ranging from 5,000 to 20,000 lux) with ambient temperatures ranging from 20 to 35 degrees Celsius and humidity levels ranging from 60 to 95 percent.

Those skilled in the art will appreciate that certain characteristics will vary with older or, conversely, with younger plants. 'HUTAAL29' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climatic, and cultural conditions. Color notations are based on The Royal Horticultural Society Colour Chart, The Royal Horticultural Society, London, third edition.

A botanical description of 'HUTAAL29' and comparisons with the parent plant and the most similar variety of common knowledge are provided below.

General plant description:

*Growth habit.*—Clumping herbaceous perennial; acaulescent, with foliage arising directly from the base of each clump.

*Plant growth habit profile.*—Vase-shaped.

*Height.*—30 cm.

*Width.*—35 cm.

*Growth rate.*—Moderately fast-growing.

*Plant vigor.*—Moderately to highly vigorous.

*Propagation.*—Method — Meristematic tissue culture. Time to initiate roots — Approximately 4 to 6 weeks to initiate roots at an average ambient temperature of 21 degrees Celsius. Crop time — Approximately 16 to 24 weeks to produce a well-rooted, marketable 10 cm container from a rooted cutting.

*Environmental tolerances.*—Moderately high tolerance to rain; moderate tolerance to wind; not drought tolerant; tolerant of temperatures to at least 40 degrees Celsius. Cold hardy to USDA Hardiness Zone 8.

*Pest resistance and susceptibility.*—Plants have not been observed to be any more or less susceptible or resistant to pathogens and pests common to *Alocasia* sp.

Root system:

*General.*—*Alocasia* sp. exhibits a shallow root system with fleshy adventitious roots arising from large corms.

*Branching.*—Freely branched.

*Density.*—Moderately dense.

*Distribution.*—Relatively shallow.

*Texture.*—Fleshy; smooth; lacking root hairs.

Stems:

*Branching characteristics.*—*Alocasia* sp. is acaulescent; not stems or lateral branches are produced.

Foliage:

*Arrangement.*—Basal foliage is alternate to spiraled.

*Division.*—Simple.

*Attachment.*—Petiolate.

*Quantity of leaves per shoot.*—7.

*Lamina.*—Shape — Narrowly hastate. Apex — Acuminate. Base — Narrowly hastate; lobes free. Aspect — Some leaves are near-flat to concave while others are slightly convex; leaves occasionally lightly spiraled. Attitude — Leaves emerge in the same plane as the petiole yet mature to oblique or pendulous. Dimensions — 12.5 cm long and 7.1 cm wide. Margin — Entire; lightly to moderately undulated. Texture and luster, adaxial surface — Rugose, glabrous, and slightly to moderately glossy. Sporadic blistering of the adaxial epidermis is present in the form of irregularly shaped, translucent-white blotches. Texture and luster, abaxial surface — Rugose, glabrous, slightly glossy. Juvenile color, adaxial surface — Mottled with light and dark shades of yellow-green, nearest to RHS 144A and 146B, respectively; colored with dark yellow-green immediately adjacent to the veins, nearest to RHS 146B; laminas are irregularly blotched with light yellow-white, nearest to RHS 158D. The amount and degree of blotching varies between leaves. Additionally, the areas of the laminar surface with epidermal blistering appear as translucent-white blotches, RHS 155A, revealing the yellow-green surface and yellow-white blotches beneath. Where epidermal blistering occurs on the yellow-green portions of the lamina, the color generally appears to be yellow-green, nearest to 147D. Juvenile color, abaxial surface — Yellow-green, nearest to RHS 144B; irregularly blotched with light yellow-white, nearest to RHS 158D. Mature color, adaxial surface — The variegation pattern and, consequently, the laminar coloration, is variable from one leaf to the next. Some laminas are predominantly dark green and contain some amount of cream white blotches, whereas other laminas are predominantly cream white, suffused or mottled with light yellow, and contain some amount of dark green blotches. Regardless of the variegation pattern and the amount of each color present, the color recitations are the same. The green coloration is nearest to a mixture of dark green and dark yellow-green, RHS 137A and 147A; the cream white coloration is nearest to orange-white RHS 158D; and the light yellow suffusion is nearest to RHS 8D. The areas of the laminar surface with epidermal blistering appear as translucent-white blotches, RHS 155A, revealing the yellow-green surface and yellow-white flecks and blotches beneath. Where epidermal blistering occurs on the yellow-green portions of the lamina, the color generally appears to be either green, nearest to 138A, or yellow-green, nearest to RHS 144B. Mature color, abaxial surface — The variegation pattern and, consequently, the laminar coloration, is variable from one leaf to the next. Some laminas are predominantly yellow-green with some amount of cream white blotches, whereas other laminas are predominantly cream white with yellow-green blotches. Additionally, some laminas have large portions of greyed-purple blotches. Regardless of the variegation pattern and the amount of each color present, the color recitations are the same. The yellow-green coloration is nearest to RHS 146D with some smaller blotches nearest to 145B. The cream white coloration is nearest to RHS 155B. The greyed-purple coloration is nearest to RHS 187B. Venation — Vein pattern — Pinnate. Vein color, adaxial surface — The main vein and lateral veins are indistinguishable on the yellow-green portions of the lamina except for those portions where epidermal blistering has occurred, in which case the veins beneath the blister will appear as a light shade of greyed-green, nearest to RHS 194D. On the cream white to light yellow portions of the lamina, the main vein and proximal portions of the lateral veins are colored greyed-purple, nearest to RHS 186B, generally appearing as pink, whereas the distal portions of the lateral veins are greyed-green, nearest to RHS 194B. Vein color, abaxial surface — On the yellow-green portions of the lamina, the lateral veins are dark yellow-green, nearest to RHS 147A. On the cream white to light yellow portions, the lateral veins are greyed-green, RHS 194B. The color of the main vein is dependent upon the amount of cream white to light yellow coloration present on the lamina. Those laminas which are predominantly yellow-green exhibit main veins that are yellow-green, nearest to RHS 148D, suffused with greyed-purple, nearest to in between RHS 183C and 183D. The main veins of leaves where approximately one-half or more of the laminar surface is colored cream white to light yellow appear as almost entirely greyed-purple, nearest to in between RHS 185D and 186C, generally appearing as a solid light pink coloration.

*Petiole*.—Attachment — Sheathed. Aspect — Subterete at the proximal end; terete at the union with the lamina. Length — Ranging from 8 to 10 cm. Width — 0.8 cm at the base. Strength — Moderately strong. Texture — Smooth and glabrous. Luster — Very slightly glossy. Color — The coloration is variable from one petiole to the next. If the lamina is predominantly green, then the petioles are longitudinally striped with near-equal amounts of both dark yellow-green, RHS 146B, and light yellow-green, RHS 148C. Laminas with a greater occurrence of the cream white to light yellow coloration exhibit petioles that are greyed-red to greyed-purple, nearest to a combination of RHS 178A and 183C. The greater the occurrence of cream white to light yellow coloration on the lamina, the more intense the greyed-purple suffusion of the petiole. Petioles of leaves where approximately one-half or more of the laminar surface or more colored cream white to light yellow appear as almost entirely greyed-purple, nearest to in between RHS 185D and 186C.

Inflorescence: *Alocasia* typically produces a spathe and spadix inflorescence, but no flowering of the claimed plant has been observed to date.

Flower buds: No flowering has been observed to date.

Flowers: No flowering has been observed to date.

Reproductive organs: No flowering has been observed to date.

Seed and fruit: Seed production has not been observed.

Comparisons with the parent: Plants of the new cultivar 'HUTAAL29' may be distinguished from the parent, an unnamed *Alocasia scalprum* plant (not patented), by the characteristics described in Table 1.

TABLE 1

Comparison Between 'HUTAAL29' and The Parent

| Characteristic | 'HUTAAL29' | The parent. |
|---|---|---|
| General coloration of the mature foliage. | Typically, dark green and irregularly flecked and blotched with a combination of cream white to light yellow. | Homogeneously dark green. |
| General coloration of the foliar veins. | Pink. | Dark green. |

Comparisons with the most similar commercial variety: Plants of the new cultivar 'HUTAAL29' may be distinguished from the most similar commercial comparator known to the inventor, *Alocasia scalprum* 'Aurea Variegata' (not patented), by the characteristics described in Table 2.

TABLE 2

Comparison Between 'HUTAAL29' and 'Aurea Variegata'

| Characteristic | 'HUTAAL29' | 'Aurea Variegata' |
|---|---|---|
| General coloration of the mature foliage. | Typically, dark green and irregularly flecked and blotched with a combination of cream white to light yellow. | Dark green and irregularly flecked and blotched with yellow. |
| General coloration of the foliar veins. | Pink. | Dark green. |

That which is claimed is:

1. A new and distinct variety of *Alocasia* plant named 'HUTAAL29', substantially as described and illustrated herein.

* * * * *